US00PP24292P3

(12) United States Plant Patent
Egger

(10) Patent No.: US PP24,292 P3
(45) Date of Patent: Mar. 4, 2014

(54) ***KNIPHOFIA* PLANT NAMED 'ORANGE VANILLA POPSICLE'**

(50) Latin Name: ***Kniphofia* spp.**
Varietal Denomination: Orange Vanilla Popsicle

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 133 days.

(21) Appl. No.: 13/507,188

(22) Filed: Jun. 12, 2012

(65) Prior Publication Data

US 2013/0333088 P1 Dec. 12, 2013

(51) Int. Cl.
*A01H 5/00* (2006.01)

(52) U.S. Cl.
USPC ..... Plt./443

(58) Field of Classification Search
None
See application file for complete search history.

(56) References Cited

PUBLICATIONS

UPOV ROM 2013/04 Citation for 'Orange Vanilla Popsicle' Oct. 15, 2012.*

* cited by examiner

*Primary Examiner* — Wendy C Haas
(74) *Attorney, Agent, or Firm* — Klarquist Sparkman, LLP

(57) ABSTRACT

A new and distinct *Kniphofia* plant characterized by its very early blooming, repeat blooming, very compact habit with multiple crowns, narrow, grassy leaves, coral red to cream-colored flowers, and excellent vigor.

1 Drawing Sheet

Botanical denomination: *Kniphofia* spp.
Cultivar designation: Orange Vanilla Popsicle.

BACKGROUND OF THE INVENTION

The present invention relates to a new and distinct *Kniphofia*, and given the cultivar name of 'Orange Vanilla Popsicle'. *Kniphofia* is in the family Asphodelaceae. 'Orange Vanilla Popsicle' is a hybrid resulting from a planned breeding program to produce a series of compact, reblooming *Kniphofia*. The cross was made using the following proprietary, unreleased plants: *Kniphofia* 17-1 (unpatented), as the seed parent, and *Kniphofia* 17-2 (unpatented), as the pollen parent. It was selected for best habit, flower color, reblooming, and crown count from many seedlings of the cross in Canby, Oreg.

Compared to *Kniphofia* 'Bressingham Comet' (unpatented), the new cultivar is more compact and free flowering with red to cream flowers rather than red orange to yellow flowers.

Compared to *Kniphofia* 'Toffee Nosed' (unpatented), the new cultivar is more compact and free flowering with red to cream flowers rather than light red to cream flowers.

SUMMARY OF THE INVENTION

The new cultivar is unique and characterized by:

1. very early blooming (flowers the first year in 30 cell plugs)
2. repeat blooming from June through September in Canby, Oreg.
3. very compact habit with multiple crowns
4. narrow, grassy leaves
5. coral red to cream colored flowers
6. excellent vigor This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a plant of a one-year-old *Kniphofia* 'Orange Vanilla Popsicle' in the ground in the trial field in July in Canby, Oreg.

DETAILED PLANT DESCRIPTION

The following is a detailed description of the new *Kniphofia* cultivar based on observations of nine-month-old specimens growing in the ground outside in part sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type.*—Rhizomatous herbaceous perennial.
*Hardiness.*—USDA Zones 6 to 9.
*Size.*—Grows to 44 cm wide and 40 cm tall from the top of the soil to the top of the foliage.
*Form.*—Upright and clumping.

Leaf:

*Type.*—Simple.

*Shape.*—Strap-like.

*Arrangement.*—Basal rosette.

*Blade size.*—Grows to 34 cm long and 10 mm wide.

*Margins.*—Entire.

*Apex.*—Acuminate.

*Base.*—Clasping.

*Surface texture.*—Glabrous on both surfaces.

*Venation.*—Parallel.

*Color.*—Top and bottom side Green 137A.

Inflorescence:

*Type.*—Spike-like scapose raceme.

*Number of flowers per raceme.*—About 100.

*Inflorescence.*—Grows to 28 cm long and 5.5 cm wide.

*Peduncle description.*—Grows to 34 cm long and 10 mm wide, glabrous, Yellow Green 146C.

*Pedicle description.*—2.5 mm long, glabrous, Yellow Green 146D.

*Bloom time.*—Late June through September in Canby, Oreg.

*Lastingness.*—An inflorescence lasts for 2 to 4 weeks depending on the temperatures.

Flower bud:

*Size.*—25 mm long and 6 mm wide.

*Shape.*—Cylindrical.

*Surface texture.*—Glabrous.

*Color.*—Changes from Red 47A to Orange Red N34C to Orange 26D with veins Orange Red N34C.

Flower:

*Type.*—Actinomorphic.

*Shape.*—Cylindrical and tubular.

*Size.*—Grows to 32 mm deep and 8 mm wide.

*Texture.*—Waxy.

*Surface texture.*—Glabrous inside and outside.

*Color.*—Inside and outside, Yellow Orange 18D with veins Orange Red N34C.

*Corolla description.*—6 lobed fused tepals, 27 mm long and 8 mm wide, each lobe 3 mm wide and 3 mm long, ovate, margin entire, tip notched; glabrous inside and out.

*Pistil description.*—One extruding, 30 mm long, ovary 3 mm long 1.8 mm wide, Yellow Green 146C, style 25 mm long, Orange 29C, stigma White NN155C.

*Stamen.*—6, 31 mm long, filaments 30 mm long, White NN155C, anthers 1.5 mm long and Yellow Orange 17A, pollen Yellow 4C.

*Fragrance.*—None.

Fruit and seed: None seen.

Pest and diseases: Pests and diseases are infrequent on *Kniphofia* spp. No problems have been observed on this plant grown under commercial conditions in Canby, Oreg.

I claim:

1. A new and distinct *Kniphofia* plant as herein shown and described.

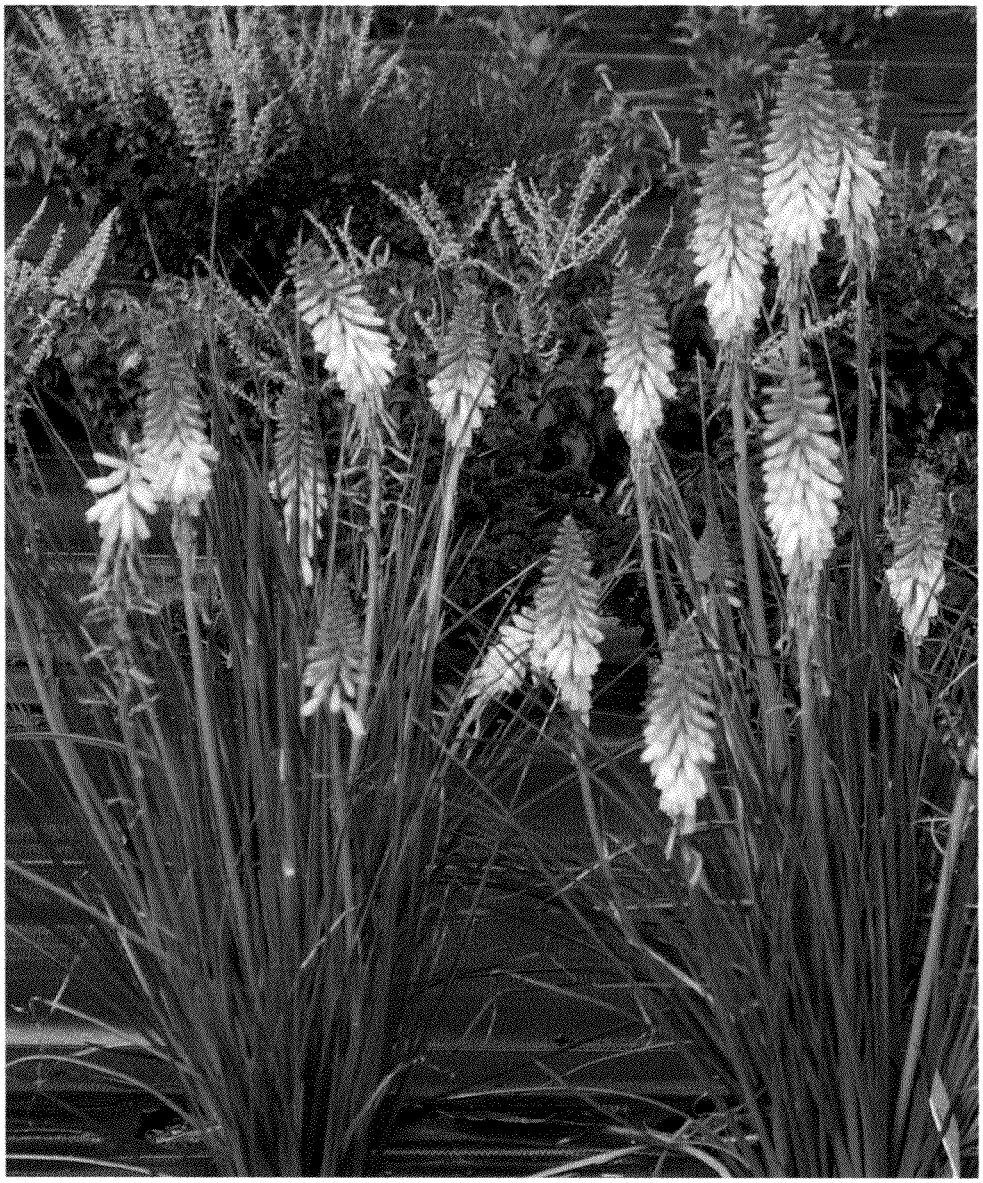

* * * * *